United States Patent
Richard

(10) Patent No.: US 7,241,455 B2
(45) Date of Patent: Jul. 10, 2007

(54) IMPLANTABLE OR INSERTABLE MEDICAL DEVICES CONTAINING RADIATION-CROSSLINKED POLYMER FOR CONTROLLED DELIVERY OF A THERAPEUTIC AGENT

(75) Inventor: Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 513 days.

(21) Appl. No.: 10/409,358

(22) Filed: Apr. 8, 2003

(65) Prior Publication Data

US 2004/0202691 A1 Oct. 14, 2004

(51) Int. Cl.
*A61F 2/00* (2006.01)
*A61K 47/30* (2006.01)

(52) U.S. Cl. .................................... 424/423; 514/772.3

(58) Field of Classification Search ................ 424/423, 424/426; 514/772.3, 772.4
See application file for complete search history.

(56) References Cited

U.S. PATENT DOCUMENTS

| | | | | |
|---|---|---|---|---|
| 4,559,117 | A * | 12/1985 | Bohm | 204/157.62 |
| 4,946,899 | A | 8/1990 | Kennedy et al. | 525/244 |
| 5,163,952 | A | 11/1992 | Froix | 623/1 |
| 5,258,020 | A | 11/1993 | Froix | 623/1 |
| 5,304,121 | A | 4/1994 | Sahatjian | 604/53 |
| 5,616,608 | A | 4/1997 | Kinsella et al. | 514/449 |
| 5,674,242 | A * | 10/1997 | Phan et al. | 606/198 |
| 5,716,981 | A | 2/1998 | Hunter et al. | 514/449 |
| 5,733,925 | A | 3/1998 | Kunz et al. | 514/449 |
| 5,741,331 | A | 4/1998 | Pinchuk | 623/11 |
| 5,789,018 | A | 8/1998 | Engelson et al. | 427/2.3 |
| 5,871,437 | A | 2/1999 | Alt | 600/3 |
| 5,871,535 | A | 2/1999 | Wolff et al. | 623/1 |
| 5,879,697 | A | 3/1999 | Ding et al. | 424/422 |
| 5,954,706 | A | 9/1999 | Sahatjian | 604/509 |
| 6,017,975 | A * | 1/2000 | Saum et al. | 522/161 |
| 6,099,562 | A | 8/2000 | Ding et al. | 623/1.46 |
| 6,113,817 | A * | 9/2000 | Herbrechtsmeier et al. | 264/1.36 |
| 6,159,142 | A | 12/2000 | Alt | 600/3 |
| 6,224,893 | B1 * | 5/2001 | Langer et al. | 424/423 |
| 6,280,411 | B1 | 8/2001 | Lennox | 604/103.05 |
| 6,335,029 | B1 | 1/2002 | Kamath et al. | 424/423 |
| 6,537,569 | B2 * | 3/2003 | Cruise | 424/426 |
| 6,545,097 | B2 | 4/2003 | Pinchuk et al. | 525/240 |
| 2002/0099438 | A1 * | 7/2002 | Furst | 623/1.16 |
| 2002/0107330 | A1 | 8/2002 | Pinchuk et al. | 525/242 |
| 2002/0197296 | A1 | 12/2002 | Gen | 424/423 |

FOREIGN PATENT DOCUMENTS

| | | |
|---|---|---|
| EP | 0623354 A1 | 11/1994 |
| EP | 1104681 A1 | 6/2001 |
| WO | WO 97/10011 | 3/1997 |
| WO | WO 98/02204 | 1/1998 |
| WO | WO 99/49908 | 10/1999 |

OTHER PUBLICATIONS www.efunda.com/units/convert_units.cfm?mode=short&From=146, Sep. 5, 2006, pp. 1,2.*
Hammerschmidt et al., "Studies of Polyvinyl Alcohol under Temperature and Humidity Control," Molecular Imaging Online, Sep. 5, 2006, pp. 1-3.*
Radiation Processing of Polymer, Radiation Processing in Your Life. http://www.geocities.com/msen20/Radprocessingofpolymers.pdf.
Karl J. Hemmerich. Polymer Materials Selection for Radiation-Sterilized Products. http://www.devicelink.com/mddi/archive/00/02/006.html.
Reference: Polymer Properties. Thermal Transitions of Homopolymers: Glass Transition & Melting Point. http://www.sigmaaldrich.com/img/assets/3900/Thermal_Transitions_of_Homopolymers.pdf.
Vestenamer: The Rubber with Unique Properties. http://www.degussa-hpp.de/dl/vestenamer_us.pdf.
Services: Crosslinking. http://www.webmpi.com/cross.html.
Physique & industrie—Radiation processing. Physique & industrie research under contract. Compact Electrostatic Accelerators. http://www.physiqueindustrie.com/_cea.htm.

* cited by examiner

*Primary Examiner*—Sharon E. Kennedy
(74) *Attorney, Agent, or Firm*—Mayer & Williams PC; David B. Bonham, Esq.

(57) ABSTRACT

An implantable or insertable medical device which comprises (a) a therapeutic agent and (b) a polymeric release region that controls the release of the therapeutic agent upon administration to a patient. The polymeric release region comprises a radiation-crosslinked polymer, and the polymeric release region is crosslinked with a radiation dose of at least 10,000 rads. The radiation-crosslinked polymer can be, for example, a radiation-crosslinked methylene-containing polymer. The polymeric release region can be, for example, (a) a carrier region that comprises the therapeutic agent or (b) a barrier region that is disposed over a therapeutic-agent-containing region that comprises the therapeutic agent. The present invention is further directed to methods of forming such medical devices, methods of releasing a therapeutic agent within a patient using such medical devices, and methods of modulating the release of a therapeutic agent from such medical devices.

36 Claims, No Drawings

IMPLANTABLE OR INSERTABLE MEDICAL DEVICES CONTAINING RADIATION-CROSSLINKED POLYMER FOR CONTROLLED DELIVERY OF A THERAPEUTIC AGENT

FIELD OF THE INVENTION

The present invention relates to implantable or insertable medical devices for controlled delivery of one or more therapeutic agents.

BACKGROUND OF THE INVENTION

Numerous medical devices have been developed for the delivery of therapeutic agents to the body.

In accordance with some delivery strategies, a therapeutic agent is provided (a) within a polymeric carrier layer and/or (b) beneath a polymeric barrier layer that is associated with an implantable or insertable medical device. Once the medical device is placed at the desired location within a patient, the therapeutic agent is released from the medical device at a rate that is dependent upon the nature of the polymeric carrier and/or barrier layer.

The desired release profile for the therapeutic agent is dependent upon the particular treatment at hand, including the specific condition being treated, the specific therapeutic agent selected, the specific site of administration, and so forth. As a result, there is a continuing need for polymeric layers, including polymeric barrier layers and carrier layers, which are able to provide a range of therapeutic agent release rates.

SUMMARY OF THE INVENTION

The present invention is directed to novel implantable or insertable medical devices, which provide controlled release of a therapeutic agent.

According to a first aspect of the present invention, the implantable or insertable medical device comprises (a) a therapeutic agent and (b) a polymeric release region that controls the release of the therapeutic agent upon administration to a patient. The polymeric release region comprises a radiation-crosslinked polymer, and the polymeric release region is crosslinked with a radiation dose of at least 10,000 rads, more typically at least 100,000 rads, even more typically 1,000,000 rads.

The polymeric release region can be, for example, (a) a carrier region that comprises the therapeutic agent or (b) a barrier region that is disposed over a therapeutic-agent-containing region that comprises the therapeutic agent.

Examples of implantable or insertable medical device include catheters, guide wires, balloons, filters, stents, stent grafts, vascular grafts, vascular patches, and shunts. The implantable or insertable medical device may be adapted for implantation or insertion, for example, into the coronary vasculature, peripheral vascular system, esophagus, trachea, colon, biliary tract, urinary tract, prostate or brain.

The therapeutic agent can be selected from any number of categories, including anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

The polymeric release region can further comprise one or more additional polymers where desired.

In some embodiments, the radiation-crosslinked polymer has a glass transition temperature that is less than, or near, ambient temperature, before crosslinking.

Radiation-crosslinked methylene-containing polymers are specific radiation-crosslinked polymers that are beneficial for use in connection with the present invention.

The methylene-containing polymer can be cyclic or linear. It can comprises, for example, (a) a plurality of $(-CH_2-)_n$ backbone groups, where n=4 or greater or (b) a plurality of $-CH=CH-$ backbone groups, for instance, where the methylene-containing polymer is the reaction product of one or more 1,3-dienes or where it is the product of an olefin metathesis reaction (e.g., the product of an acyclic diene metathesis polymerization reaction or a ring opening metathesis polymerization reaction).

The methylene-containing polymer can also be the product of a copolymerization reaction comprising (a) an acyclic unsaturated hydrocarbon monomer (which can be, for example, an alpha olefin) and (b) an additional monomer (which can be selected from, for example, acrylic monomers, aminoalkyl methacrylate monomers, vinyl ether monomers, cyclic ether monomers, unsaturated ester monomers, and halogenated unsaturated hydrocarbon monomers). As a specific example, the acyclic unsaturated monomer can be ethylene and the additional monomer can be an alkyl acrylate. The copolymer can be, for example, a random copolymer, a block copolymer, a graft copolymer or an alternating copolymer.

According to another aspect of the invention, a method of releasing a therapeutic agent within a patient is provided, which comprises: (a) providing an implantable or insertable medical device like those described herein, and (b) implanting or inserting the implantable or insertable medical device into a patient. For example, the medical device may be implanted or inserted into the coronary vasculature, peripheral vascular system, esophagus, trachea, colon, biliary tract, urinary tract, prostate or brain of the patient. As a more specific example, the medical device may be inserted into the vasculature of the patient, for example, to release a therapeutic agent for the treatment of restenosis.

According to yet another aspect of the present invention, a method of providing an implantable or insertable medical device like those described herein is provided, which comprises: (a) applying a coating comprising a methylene-containing polymer on a surface of an implantable or insertable medical device; and (b) exposing the coating to a radiation dose of at least 10,000 rads, more typically at least 100,000 rads, even more typically 1,000,000 rads. The radiation dose can be provided using a variety of radiation types, including gamma ray radiation and electron beam radiation. In some embodiments, the rate of release of the therapeutic agent from the medical device is modulated by modifying the crosslinking radiation dose that is applied.

One advantage of the present invention is that implantable or insertable medical devices can be provided, which provide for controlled release of a therapeutic agent.

Another advantage of the present invention is that such devices can be provided using radiation crosslinking techniques, which are clean and inexpensive.

Another advantage of the present invention is that the drug release profile associated with such devices can be altered by modifying the dosage of the radiation that is applied, avoiding the need to reformulate the chemical composition of the release region.

Yet another advantage of the present invention is that, because radiation crosslinking is used, there is no need to add chemical crosslinking agents, which can act as impurities in the release region that is formed.

These and other embodiments and advantages of the present invention will become immediately apparent to those of ordinary skill in the art upon review of the Detailed Description and claims to follow.

DETAILED DESCRIPTION OF THE INVENTION

According to an embodiment of the present invention, an implantable or insertable medical device is provided, which comprises (a) a therapeutic agent and (b) a polymeric release region that controls the release of the therapeutic agent upon administration to a patient. The radiation-crosslinked polymeric release region is typically crosslinked with a radiation dose of at least 10,000 rads (0.01 Mrad), more typically at least 100,000 rads (0.1 Mrad), and more typically at least 1,000,000 rads (1 Mrad). The radiation-crosslinked polymeric release region is formed from any radiation sensitive polymer that can give rise to reactive species, which in turn produce crosslinking reactions, when exposed to ionizing radiation (such polymers are referred to herein as "radiation-crosslinkable polymers"). For example, the radiation-crosslinked polymeric release region may be formed from a methylene-containing polymer, (i) which can have an elogation at break of at least 25% at ambient temperature, (ii) which can be crystalline or amorphous or both, at ambient temperature, before crosslinking, and (iii) which can have a glass transition temperature less than or near ambient temperature.

By "release region" is meant a region that regulates the rate of release of a therapeutic agent. Release regions are commonly either carrier regions or barrier regions. A "carrier region" is region which contains at least one therapeutic agent and from which the therapeutic agent is released. A "barrier region" is a region which is disposed between a source of therapeutic agent and a site of intended release and which controls the rate at which the therapeutic agent is released.

The polymeric release region can be present in the medical device in a number of configurations. For example, the polymeric release region can constitute the entirety of the medical device, or it can constitute only a portion of the medical device. The portion of the medical device can be, for example, (a) one or more medical device layers (e.g., one or more coating layers), (b) one or medical device components or portions thereof, and so forth.

For example, in some embodiments of the present invention, an outer carrier layer is disposed over at least a portion of an implantable or insertable medical device. Upon implantation or insertion of the device into a patient, the therapeutic agent is released from the carrier layer in a controlled fashion. In other embodiments, a therapeutic-agent-containing layer and a barrier layer are disposed over at least a portion of an implantable or insertable medical device. The barrier layer is disposed over the therapeutic-agent-containing layer. As a result, the barrier layer acts to control release of the therapeutic agent from the medical device upon implantation or insertion of the same.

Preferred implantable or insertable medical devices for use in conjunction with the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the localized treatment of any mammalian tissue or organ. Non-limiting examples are tumors; organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone.

One particularly preferred medical device for use in connection with the present invention is a vascular stent, which delivers therapeutic agent into the vasculature for the treatment of restenosis. As used herein, "treatment" refers to the prevention of a disease or condition, the reduction or elimination of symptoms associated with a disease or condition, or the substantial or complete elimination a disease or condition. Preferred subjects (i.e., patients) are mammalian subjects and more preferably human subjects.

The radiation-crosslinkable polymer within the polymeric release region of the medical devices of the present invention beneficially has an elongation at break of at least 25% at ambient temperature. "Elongation" is an increase in length of a test specimen under tension, stated herein as a percentage of the original length. The "elongation at break" is the amount of elongation that is observed at the point where the specimen breaks or otherwise fails under tension. Ambient temperature is typically 25° C.–45° C., more typically body temperature (e.g., 35° C.–40° C.).

The radiation-crosslinkable polymer may have a glass transition temperature near or less than ambient temperature, before crosslinking, more typically less than 30° C., 20° C., 0° C., −20° C., −40° C. or even less than −60° C.

Beneficial polymers for use in connection with the present invention are methylene-containing polymers. A "methylene-containing polymer" is a polymer that contains a plurality of $(-CH_2-)_n$ groups along a chain within the polymer, where n is an integer of one or greater. Typically, the methylene-containing polymers used in connection with the present invention will be formed from 10 or more monomers, more typically 50, 100, 500 or even more monomers.

The methylene-containing polymers used in connection with the present invention may be provided in a variety of configurations, including cyclic, linear and branched configurations. Branched configurations include star-shaped configurations (e.g., configurations in which three or more chains emanate from a single branch point), comb configurations (e.g., graft polymers having a main chain and a plurality of branching side chains), and dendritic configurations (including arborescent or hyperbranched polymers). They can be formed from a single monomer (i.e., they can be homopolymers), or they can be formed from multiple monomers (i.e., they can be copolymers), which can be distributed, for example, randomly, in an orderly fashion (e.g., in an alternating fashion), or in blocks.

Typically, the methylene-containing polymers are formed using one or more unsaturated hydrocarbon monomers, such as linear, branched and cyclic alkenes. Examples include ethylene and other alpha-olefins (e.g., $C_3$–$C_{20}$ alpha-olefins, which can be branched or unbranched, such as propene, 1-butene, 1-pentene, 4-methyl pentene, 1-hexene, 1-heptene, 1-octene and 1-octadecene), diolefins (e.g., trans-butadiene, cis-isoprene and trans-isoprene), and cyclic olefins (e.g., $C_4$–$C_{20}$ cycloolefins such as cyclobutene, cyclopentene, cyclohexene, cyclooctene, etc.).

A number of chemical synthesis techniques are known for polymerization of unsaturated hydrocarbon monomers, including free-radical polymerization, cationic polymerization, anionic polymerization, Ziegler-Natta polymerization, metallocene polymerization, nitroxide-mediated polymerization (NMP), atom transfer radical polymerization (ATRP), reversible addition-fragmentation chain transfer (RAFT) polymerization, and olefin metathesis polymerization.

In many embodiments the methylene-containing polymer will include groups in addition to the plurality of (—$CH_2$—)$_n$ groups.

In some embodiments, for example, the methylene-containing polymer includes a plurality of —CH═CH— groups in addition to the plurality of (—$CH_2$—)$_n$ groups.

—CH═CH— groups can be introduced using a number of methods. As one example, a copolymer can be formed that contains an acyclic unsaturated hydrocarbon monomer (e.g., ethylene or an alpha olefin) and a monomer with a —C≡C— group (e.g., acetylene).

As another specific example, 1,3-dienes (e.g., butadiene or isoprene) can be polymerized using known techniques, for example, Ziegler-Natta polymerization to yield unsaturated polymers, for example, polyisoprene,

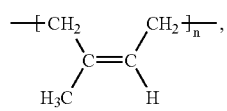

and polybutadiene,

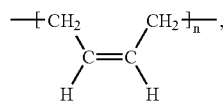

where n is an integer. Cis-isoprene has a $T_g$ of around –63° C., trans-isoprene has a $T_g$ of around –66° C., and cis-butadiene has a $T_g$ of around –58° C. Trans-butadiene has a $T_g$ of around 102° C. and is therefore less desirable for this reason. These polymers are examples of methylene-containing polymers having a plurality of (—$CH_2$—)$_n$ groups, where n is 2, and a plurality of >C═C< groups as well.

Another specific example is metathesis polymerization of an acyclic diene, for example, a 1-(n-1) $C_n$-diene, such as 1–4 pentadiene, 1–5 hexadiene, 1–7 octadiene, and so forth. For example the metathesis polymerization of 1–5 hexadiene yields:

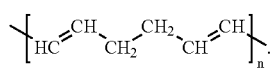

This polymer is an example of a methylene-containing polymers having a plurality of (—$CH_2$—)$_n$ groups, where n is 2, and a plurality of >C═C< groups as well.

Yet another specific example, is ring opening metathesis polymerization of a cyclic olefin (e.g., $C_4$–$C_{20}$ cycloolefins such as cyclobutene, cyclopentene, cyclohexene, cyclooctene, etc.). One commercially available ring opening metathesis polymerization product is sold under the name Vestenamer® by Degussa Corp., Parsippany, N.J. Vestenamer® is a mixture of cyclic and linear polyoctenamers, which can be represented by the following:

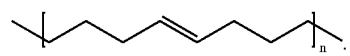

These polymers are examples of methylene-containing polymers having a plurality of (—$CH_2$—)$_n$ groups, where n is 6, and a plurality of >C═C< groups as well. During production, cyclooctene is polymerized in a metathesis reaction to produce a mixture of the cyclic and linear forms of the polyoctenamer illustrated. The cis/trans ratio, which determines the crystallinity of the final product, is controlled by the polymerization conditions. Two specific commercially available products are Vestenamer® Grade 8012, which has a crystallinity at 23° C. of 30%, a melting point of 54° C. and a glass transition temperature of –65° C. and Vestenamer® Grade 6213, which has a crystallinity at 23° C. of 10%, a melting point of < 36° C. and a glass transition temperature of –75° C.

In other embodiments, groups in addition to the plurality of (—$CH_2$—)$_n$ groups, are introduced into the methylene-containing polymer by polymerization in the presence of a monomer that is not an unsaturated hydrocarbon monomer. For example, a copolymer can be formed by polymerizing an unsaturated hydrocarbon monomer along with one or more of the following monomers: (a) acrylic monomers such as alkyl acrylates (e.g., methyl acrylate, ethyl acrylate, propyl acrylate, isopropyl acrylate, butyl acrylate, sec-butyl acrylate, tert-butyl acrylate, isobutyl acrylate, hexyl acrylate, cyclohexyl acrylate, 2-ethylhexyl acrylate, dodecyl acrylate, and hexadecyl acrylate), halo-alkyl acrylates (e.g., 2,2,2-trifluoroethyl acrylate), cyano-alkyl acrylates (e.g., 2-cyanoethyl acrylate), and alkoxyalkyl acrylates (e.g., 2-methoxyethyl acrylate and 2-ethoxyethyl acrylate), (b) methacrylates such as aminoalkyl methacrylates (e.g., diethylaminoethyl methacrylate and 2-tert-butyl-aminoethyl methacrylate), (c) vinyl ethers such as alkyl vinyl ethers (e.g., methyl vinyl ether, ethyl vinyl ether, propyl vinyl ether, butyl vinyl ether, isobutyl vinyl ether, 2-ethylhexyl vinyl ether and dodecyl vinyl ether), (d) cyclic ethers such as tetrahydrofuran, trimethylene oxide, ethylene oxide, propylene oxide, methyl glycidyl ether, butyl glycidyl ether, allyl glycidyl ether, epibromohydrin, epichlorohydrin, 1,2-epoxybutane, 1,2-epoxyoctane and 1,2-epoxydecane, (e) additional esters such as ethylene adipate, tetramethylene adipate, ethylene malonate, vinyl acetate, vinyl propionate and vinyl trifluoroacetate, (f) halogenated unsaturated hydrocarbons, such as vinyl fluoride, vinylidene chloride, vinylidene fluoride, cis-chlorobutadiene, trans-chlorobutadiene, and (g) other monomers including ε-caprolactone, 1-vinyl-2-pyrrolidone and methyl styrene. The copolymer can be a random, alternating or block copolymer, typically a random or alternating copolymer.

Some specific examples of copolymers include random copolymers of: (a) ethylene and butyl acrylate, available commercially from Aldrich, (b) ethylene and methyl acrylate, available commercially from Aldrich, and (c) ethylene, methyl acrylate and acrylic acid available commercially from Aldrich.

Without wishing to be bound by theory, it is believed that a primary mechanism by which the methylene-containing polymers are crosslinked proceeds from the CH bond scission that occurs as a result of the high-energy radiation. This results in the formation of free radicals, which can combine with one another. Where the free radicals are on the same polymer molecule, an intermolecular crosslink will be formed. Where the free radicals are on different polymer molecules, an intramolecular crosslink will be formed. Where the polymer includes carbon-carbon double bonds, similar reactions arise from free radicals that are formed from the scission one of these bonds.

So long as it is of sufficiently high energy, essentially any type of radiation can be used to crosslink the radiation-crosslinkable polymers within the release regions of the present invention. Preferred sources of high-energy radiation include gamma rays, X rays, and electron beams.

To achieve the desired degree of crosslinking, the radiation dosages used in connection with the present invention are typically at least 0.01 Mrad, more typically at least 0.1 Mrad and more typically at least 0.25 Mrad. Specific examples include ranges of 0.25 Mrad to 50 Mrad, 0.5 Mrad to 30 Mrad, 1 Mrad to 25 Mrad, and 10 Mrad to 20 Mrad.

As previously noted, radiation crosslinking is clean and inexpensive. Moreover, the crosslink density, and hence the release characteristics of the medical device, can be changed by merely modifying the dose of the radiation that is applied. As a result, the release characteristics can be modified without an attendant change in composition, which is commonly required.

In addition, crosslinking is achieved without the need for crosslinking agents, which can represent a potential source of impurity in the crosslinked product. Nonetheless, if desired, reactive gases, liquids or solids can be provided within the device during irradiation to initiate other chemical reactions that could affect the elution rate of the therapeutic agent or to create a unique chemical surface on the coating (e.g., a lubricious coating, an anti-thrombogenic coating, etc.)

The crosslinking radiation dosages used in connection with the present invention can also be sufficiently high to sterilize the medical device in some embodiments. This is advantageous for therapeutic agents that are not compatible with ethylene oxide or other modes of sterilization, which involve the application of heat, moisture and/or reactive chemicals.

Prior to crosslinking, the device or device portion to which the release region corresponds (for example, a device coating, a device component, or an entire device) can be formed using a number of known techniques.

For example, where the components of the polymeric release region have thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths. One example of a polymer with thermoplastic characteristics is Vestenamer® Grade 8012, which has a melting point of about 54° C.

As one specific example, an entire stent structure can be extruded using the above techniques. As another example, a coating can be provided by extruding a coating layer onto a pre-existing stent. As yet another example, a coating can be co-extruded along with an underlying stent structure.

If the therapeutic agent is also stable under processing conditions, then it can be combined with the polymer prior to thermoplastic processing to produce a therapeutic-agent-containing carrier region. If not, then a therapeutic-agent-containing carrier region can be formed by post-processing introduction of therapeutic agent as discussed below.

In other embodiments, the polymeric release region is formed using solvent-based techniques in which the components of the polymeric release region are first dissolved in a solvent system that contains one or more solvent species, and the resulting mixture is subsequently used to form the polymeric release region.

The solvent system that is selected is preferably a good solvent for the component(s) of the polymeric release region and, where included, for the therapeutic agent as well. The particular solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension such as air suspension, ink jet techniques, electrostatic techniques, and combinations of these processes.

Where solvent-based processing is employed, the mixture containing the solvent(s) and the component(s) of the polymeric release region (e.g., a methylene-containing polymer such as Vestenamer®) is preferably applied to a substrate to form the release region.

In some embodiments, the substrate is all or a portion of an implantable or insertable medical device to which the release layer is applied. In other embodiments, the substrate is a template from which the polymeric release region is removed after solvent elimination. Such template-based techniques are particularly appropriate for forming simple objects such as sheets, tubes, cylinders and so forth, which can be easily removed from a template substrate. In other techniques, for example, fiber forming techniques, the polymeric release region is formed without the aid of a substrate or template.

Where appropriate, techniques such as those listed above can be repeated or combined to build up a release region to a desired thickness. The thickness of the release region can be varied in other ways as well. For example, in solvent spraying, thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be included in the polymer mixture and hence co-established with the carrier region. In other embodiments, the therapeutic agent is introduced into a previously formed release region. For example, the therapeutic agent can be dissolved within a solvent, and the resulting solution contacted with the previously formed release region using, for example, one or more of the application techniques described above (e.g., dipping, spraying, etc.).

As previously noted, barrier layers can be formed over a therapeutic-agent-containing region. In some embodiments, the therapeutic-agent-containing region will comprise one or more polymers, which can be selected, for example, from the polymers described elsewhere in this application. In these instances, the therapeutic-agent-containing region can be established, for example, using the solvent-based techniques (e.g., dipping, spraying, etc.) that are discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be applied to a substrate again using, for example, one or more of the application techniques described above (e.g., dipping, spraying, etc.).

Where a release region is formed using a solvent based technique, it is preferably dried after application to remove the solvents. Where the release region is a release layer coated on an underlying medical device, the release layer typically further conforms to the underlying medical device during the drying process.

In forming the polymeric release regions of the present invention, one or more radiation crosslinked polymers can be provided, as desired. In addition to the radiation-crosslinked polymer (e.g., methylene-containing polymer), polymers can be added, for example, to influence the strength or diffusion properties of the release layer.

The polymers may be, for example, homopolymers or copolymers, crosslinked or uncrosslinked, linear or branched, natural or synthetic, thermoplastic or thermosetting. Polymers include the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and poly isobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as combinations and copolymers of the above.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o) agents that interfere with endogenous vasoactive mechanisms.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include (a) plasmids, (b) viral vectors such as adenovirus, adenoassociated virus and lentivirus, and (c) non-viral vectors such as lipids, liposomes and cationic lipids.

Cells for use in connection with the present invention include cells of human origin (autologous or allogeneic), including stem cells, or from an animal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (O) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

Medical devices having a sustained release profile are beneficial in many cases. By "sustained release profile" is meant a release profile in which less than 25% of the total release from the medical device that occurs over the course of implantation/insertion in the body occurs within the first 1, 2, 3 or even more days of administration. Conversely, this means that more than 75% of the total release from the medical device will occur after the device has been implanted/inserted for the same period.

The release characteristics associated with the release layers of the present invention can be modified in a number of ways, including the following: (a) varying the type, molecular weight and/or relative amount of the radiation-crosslinked polymer, (b) providing one or more polymers within the release layer in addition to the radiation-crosslinked polymer, (c) varying the porosity of the release region, and (d) where solvent-based techniques are used to form the release region, varying the type and relative amounts of solvents used in processing the polymeric release region. The release of therapeutic agent can also be controlled, for example, by varying the release region thickness. Moreover, multiple release regions can be employed to achieve this end. In addition, where a carrier region is employed, a therapeutic-agent concentration gradient can be established within the carrier region to control release of therapeutic agent.

However, the release characteristics of the release layers are typically modified by varying the dosage of the radiation that is used (and hence the degree of crosslinking that is obtained), thus avoiding the need to reformulate the chemical composition of the release region.

The invention is further described with reference to the following non-limiting Examples.

EXAMPLE 1

A solution is provided that contains (a) 25 wt % tetrahydrofuran (THF), (b) 74 wt % toluene, (c) 0.25 wt % paclitaxel and (d) 0.75 wt % Vestenamer® 6213 or Vestenamer® 8012, which are mixtures of linear and cyclic polyoctenamers by Degussa Corp., Parsippany, N.J. All solutions are prepared by (1) mixing the paclitaxel and tetrahydrofuran, (2) adding the polymer, (3) adding the toluene, (4) thoroughly mixing (e.g., overnight), and (5) filtering.

The solution is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying, such that the nozzle moves along the component while spraying for one or more passes. After a carrier coating is formed in this fashion, the stent is dried, for example, by placing it in a preheated oven.

32 stents are formed in this manner for each of the Vestenamer® 6213 and Vestenamer® 8012 coatings. Of these, 8 stents act as a control, 8 are subjected to 5 Mrad crosslinking radiation, 8 are subjected to 10 Mrad crosslinking radiation, and 8 are subjected to 15 Mrad crosslinking radiation. Microscopic evaluation indicated that coating quality was good for all radiation doses.

EXAMPLE 2

A solution is provided that contains (a) 25 wt % tetrahydrofuran (THF), (b) 74 wt % toluene, (c) 0.25 wt % paclitaxel and (d) 0.75 wt % poly(ethylene-co-butyl acrylate) copolymer available from Aldrich. Solutions are prepared by (1) mixing the copolymer with the toluene and heating to 70° C. for about an hour, (2) adding the THF, (3) adding the paclitaxel, (4) thoroughly mixing (e.g., overnight), and (5) filtering.

The solution is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying, such that the nozzle moves along the stent while spraying for one or more passes. After a carrier coating is formed in this fashion, the stent is dried, for example, by placing it in a preheated oven.

32 stents are formed in this manner. Of these, 8 stents act as a control, 8 are subjected to 2.5 Mrad crosslinking radiation, 8 are subjected to 5 Mrad crosslinking radiation, and 8 are subjected to 10 Mrad crosslinking radiation. Microscopic evaluation indicated that coating quality was good for all radiation doses.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising (a) a therapeutic agent and (b) a polymeric release region that controls the release of said therapeutic agent upon administration to a patient, wherein said polymeric release region comprises a radiation-crosslinked polymer that is crosslinked without a crosslinking agent, wherein said radiation-crosslinked polymer is a radiation-crosslinked methylene-containing polymer that is formed from one or more hydrocarbon monomers and wherein said polymeric release region is crosslinked with a radiation dose of at least 10,000 rads.

2. The implantable or insertable medical device of claim 1, wherein said polymeric release region is crosslinked with a radiation dose of at least 100,000 rads.

3. The implantable or insertable medical device of claim 1, wherein said polymeric release region is crosslinked with a radiation dose of at least 1,000,000 rads.

4. The implantable or insertable medical device of claim 1, wherein said polymeric release region is a carrier region that comprises said therapeutic agent.

5. The implantable or insertable medical device of claim 1, wherein said polymeric release region is a barrier region disposed over a therapeutic-agent-containing region that comprises said therapeutic agent.

6. The implantable or insertable medical device of claim 1, wherein said polymeric release region is in the form of a coating layer.

7. The implantable or insertable medical device of claim 1, wherein said implantable or insertable medical device is selected from a catheter, a guide wire, a balloon, a filter, a stent, a stent graft, a vascular graft, a vascular patch, and a shunt.

8. The implantable or insertable medical device of claim 1, wherein said implantable or insertable medical device is adapted for implantation or insertion into the coronary vasculature, peripheral vascular system, esophagus, trachea, colon, biliary tract, urinary tract, prostate or brain.

9. The implantable or insertable medical device of claim 1, wherein said therapeutic agent is selected from one or more of the group consisting of an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms.

10. The implantable or insertable medical device of claim 1, wherein said polymeric release region has an elongation at break of at least 25% at ambient temperature.

11. The implantable or insertable medical device of claim 1, wherein said methylene-containing polymer has a glass transition temperature that is less than ambient temperature, before crosslinking.

12. The implantable or insertable medical device of claim 1, wherein said methylene-containing polymer comprises a plurality of (—$CH_2$—)$_n$ backbone groups, where n=4 or greater.

13. The implantable or insertable medical device of claim 1, wherein said polymeric release region comprises a cyclic methylene-containing polymer.

14. The implantable or insertable medical device of claim 1, wherein said methylene-containing polymer further comprises a plurality of —CH=CH— backbone groups.

15. The implantable or insertable medical device of claim 14, wherein said methylene-containing polymer is the reaction product of one or more 1,3-dienes.

16. The implantable or insertable medical device of claim 14, wherein said methylene-containing polymer is the product of an olefin metathesis reaction.

17. The implantable or insertable medical device of claim 16, wherein said methylene-containing polymer is the product of an acyclic diene metathesis polymerization reaction or a ring opening metathesis polymerization reaction.

18. The implantable or insertable medical device of claim 1, wherein said methylene-containing polymer is the product of a copolymerization reaction comprising (a) an acyclic unsaturated hydrocarbon monomer, and (b) an additional monomer.

19. The implantable or insertable medical device of claim 18, wherein said additional monomer is selected from acrylic monomers, aminoalkyl methacrylate monomers, vinyl ether monomers, cyclic ether monomers, unsaturated ester monomers, and halogenated unsaturated hydrocarbon monomers.

20. The implantable or insertable medical device of claim 18, wherein said acyclic unsaturated monomer is an alpha olefin.

21. The implantable or insertable medical device of claim 18, wherein said copolymer is selected from a random copolymer, a block copolymer, a graft copolymer and an alternating copolymer.

22. The implantable or insertable medical device of claim 18, wherein said acylic unsaturated monomer is ethylene and wherein said additional monomer is an alkyl acrylate.

23. The implantable or insertable medical device of claim 1, wherein said polymeric release region further comprises an additional polymer.

24. A method of forming the implantable or insertable medical device of claim 1, comprising: (a) applying a coating comprising said methylene-containing polymer on a surface of an implantable or insertable medical device; and (b) exposing said coating to a radiation dose of at least 10,000 rads.

25. The method of claim 24, wherein said radiation dose of at least 100,000 rads.

26. The method of claim 24, wherein said radiation dose of at least 1,000,000 rads.

27. The method of claim 24, wherein said radiation dose is provided by gamma ray or electron beam radiation.

28. The method of claim 24, wherein the rate of release of the therapeutic agent from the medical device is modulated by modifying the crosslinking radiation dose.

29. The method of claim 24, wherein said coating is applied over a therapeutic-agent-containing region that comprises said therapeutic agent.

30. A method of releasing a therapeutic agent within a patient comprising (a) providing the implantable or insertable medical device of claim 1 and (b) implanting or inserting the implantable or insertable medical device into a patient.

31. The method of claim 30, wherein said medical device is selected from a catheter, a guide wire, a balloon, a filter, a stent, a stern graft, a vascular graft, a vascular patch, and a shunt.

32. The method of claim 31, wherein said medical device is inserted into the vasculature.

33. The method of claim 32, wherein said therapeutic agent is released in the treatment of restenosis.

34. The method of claim 30, wherein the rate of release of the therapeutic agent from the medical device upon implantation or insertion of the device into a patient corresponds to a sustained release profile.

35. The method of claim 12, wherein said methylene-containing polymer comprises >C=C< groups in addition to said (—$CH_2$—)$_n$ groups.

36. The implantable or insertable medical device of claim 12, wherein said methylene-containing polymer is

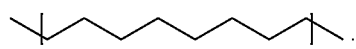

* * * * *

UNITED STATES PATENT AND TRADEMARK OFFICE
CERTIFICATE OF CORRECTION

PATENT NO. : 7,241,455 B2  
APPLICATION NO. : 10/409358  
DATED : July 10, 2007  
INVENTOR(S) : Robert E. Richard Page 1 of 1

It is certified that error appears in the above-identified patent and that said Letters Patent is hereby corrected as shown below:

Specification, Col. 1, Line 52, after "medical", change "device" to -- devices --.

Specification, Col. 2, Line 10, after "can", change "comprises" to -- comprise --.

Specification, Col. 3, Line 28-29, after "an", change "elogation" to -- elongation --.

Specification, Col. 3, Line 37, after "is", insert -- a --.

Specification, Col. 4, Line 27, after "elimination", insert -- of --.

Specification, Col. 5, Line 27-28, change "-C C-" to -- -C≡C- --.

Specification, Col. 7, Line 16, after "scission", insert -- of --.

Specification, Col. 8, Line 8, after "of", insert -- a --.

Specification, Col. 13, Line 25, after "of", insert -- the --.

Signed and Sealed this

Twenty Second Day of April, 2008

JON W. DUDAS  
*Director of the United States Patent and Trademark Office*